United States Patent
Lee et al.

(10) Patent No.: US 11,253,566 B2
(45) Date of Patent: Feb. 22, 2022

(54) **COMPOSITION FOR AMELIORATING, OR TREATING DEPRESSION AND ANXIETY DISORDER COMPRISING *FRAXINUS RHYNCHOPHYLLA* EXTRACT AS EFFECTIVE INGREDIENT**

(71) Applicant: KOREA INSTITUTE OF ORIENTAL MEDICINE, Daejeon (KR)

(72) Inventors: Mi Young Lee, Seoul (KR); Yu Ri Kim, Daejeon (KR); Bo-Kyung Park, Daejeon (KR); Young Hwa Kim, Gyeonggi-do (KR)

(73) Assignee: KOREA INSTITUTE OF ORIENTAL MEDICINE, Daejeon (KR)

( * ) Notice: Subject to any disclaimer, the term of this patent is extended or adjusted under 35 U.S.C. 154(b) by 29 days.

(21) Appl. No.: 16/755,338

(22) PCT Filed: Oct. 15, 2018

(86) PCT No.: PCT/KR2018/012074
§ 371 (c)(1),
(2) Date: Apr. 10, 2020

(87) PCT Pub. No.: WO2019/078555
PCT Pub. Date: Apr. 25, 2019

(65) Prior Publication Data
US 2020/0306330 A1  Oct. 1, 2020

(30) Foreign Application Priority Data
Oct. 16, 2017 (KR) .................... 10-2017-0134156

(51) Int. Cl.
| | | |
|---|---|---|
| *A61K 36/63* | (2006.01) | |
| *A23L 33/105* | (2016.01) | |
| *A23L 33/00* | (2016.01) | |
| *A61P 25/22* | (2006.01) | |
| *A61P 25/24* | (2006.01) | |

(52) U.S. Cl.
CPC ............ *A61K 36/63* (2013.01); *A23L 33/105* (2016.08); *A23L 33/40* (2016.08); *A61P 25/22* (2018.01); *A61P 25/24* (2018.01); *A23V 2002/00* (2013.01); *A61K 2236/33* (2013.01); *A61K 2236/331* (2013.01)

(58) Field of Classification Search
None
See application file for complete search history.

(56) References Cited

U.S. PATENT DOCUMENTS 10,709,750 B2 * 7/2020 Lee .................. A23L 33/105

FOREIGN PATENT DOCUMENTS

| CN | 103007111 A | 4/2013 |
|---|---|---|
| CN | 105497528 A | 4/2016 |
| CN | 107334863 | * 11/2017 |
| JP | 2004-083449 A | 3/2004 |
| KR | 2007 103629 | * 10/2007 |
| KR | 10-2009-0072858 A | 7/2009 |

OTHER PUBLICATIONS

International Search Report for PCT/KR2018/012074 dated May 9, 2019.
Naert, G., et al. "Brain-derived neurotrophic factor and hypothalamic-pituitary-adrenal axis adaptation processes in a depressive-like state induced by chronic restraint stress", Molecular and Cellular Neuroscience, vol. 46, pp. 55-66, 2011.
Martin, M. J. et al., "Esculine, Ranitidine and Carbenoxolone: Different Modes of Action on Gastric Mucosa", Genera Pharmacology, vol. 22, No. 6, pp. 1001-1004, 1991.
Kim, Il Hyuk et al., "The Chemical Constituents and Their Pharmacological Activities of Endemic Medicinal Plants in Korea", Korean Journal of Pharmacognosy, vol. 24, No. 3, pp. 197-202, 1993 (English translation of abstract is submitted herewith.).
Hong, Yong Deog et al., "Depigmenting Effects of Esculetin and Esculin Isolated from Fraxinus rhynchophyllaHance", J. Soc. Cosmet. Scientists Korea, vol. 40, No. 1, pp. 89-94, 2014.
Kunjbihari Sulakhiya et al., "Lipopolysaccharide induced anxiety- and depressive-like behaviour in mice are prevented by chronic pre-treatment of esculetin", Neuroscience Letters, vol. 611, pp. 106-111, 2016.

* cited by examiner

*Primary Examiner* — Ralph J Gitomer
(74) *Attorney, Agent, or Firm* — The PL Law Group, PLLC

(57) ABSTRACT

A method for preventing or treating at least one of depression and anxiety disorder according to an embodiment of the present invention includes administering to a subject in need thereof a composition having an extract of *Fraxinus rhynchophylla* as an effective ingredient. By having an effect of improving depressive behavior and low physical activity shown in an animal model with induced anxiety and depression, reducing the level of cortisol, increasing the level of serotonin, and also increasing the expression amount of pCERB, BDNF, and mBDNF proteins in hippocampal tissues, the compositions can be advantageously used for developing a functional health food product or a pharmaceutical product for ameliorating or treating the depression and anxiety disorder.

19 Claims, 12 Drawing Sheets
Specification includes a Sequence Listing.

COMPOSITION FOR AMELIORATING, OR TREATING DEPRESSION AND ANXIETY DISORDER COMPRISING *FRAXINUS RHYNCHOPHYLLA* EXTRACT AS EFFECTIVE INGREDIENT

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2018/012074 filed on Oct. 15, 2018, which claims priority to the benefit of Korean Patent Application No. 10-2017-0134156 filed in the Korean Intellectual Property Office on Oct. 16, 2017, the entire contents of which are incorporated herein by reference.

TECHNICAL FIELD

The present invention relates to a composition for preventing, ameliorating, or treating depression and anxiety disorder comprising *Fraxinus rhynchophylla* extract as an effective ingredient.

BACKGROUND ART

Depression is a common mental illness which is also called a "cold of the soul". It is a brain disorder which may cause a troublesome social relationship, and, in severe case, may result in devastating outcomes such as suicide. Fortunately, depression is a disorder that can be effectively treated, and it is a medical disorder having early recovery rate of 70 to 80% within 2 months. Counseling and psychotherapy are essentially required for treating depression, and, for a treatment of moderate to severe depression, administration of an anti-depressant is also necessarily required. In particular, the recently-developed anti-depressants can improve the depression symptoms by increasing the low serotonin in brain, and, as having almost no side effect, they can safely ameliorate the depression. Depression has a variety of causes, but, when it occurs due to a biological cause, it is based on an imbalance among the neurotransmitters present in brain. As a representative example of the neurotransmitter, histamine, serotonin, dopamine, and the like can be mentioned. It is generally known that a decrease in cerebral neurotransmitter named serotonin is highly related to depression. Depression can be also caused by life or environmental stress, and stress from death of loved ones, separation from them, loneliness, unemployment, or financial troubles may induce or aggravate the depression, and it may be also caused by a physical disorder, a drug, or the like. For example, various disorders like cancer, an endocrinal disorder, a stroke accompanying acute unconsciousness and paralysis, which is caused by a blood circulation problem in brain, and the like may cause the depression.

Anxiety disorder broadly represents a mental disorder having troubles in everyday life due to abnormal, chronic anxiety and fear in various forms. Although the anxiety and fear belong to the normal emotional response, once they are over the normal range, a mental pain and physical symptoms are exhibited. As the sympathetic nerves are stimulated by anxiety, physical symptoms such as headache, fast heartbeat, rapid and shallow breathing, or a trouble in gastrointestinal tract are shown to yield an uncomfortableness, and, when it becomes difficult to perform an everyday activity in family life, work life, and study, it can be diagnosed as an anxiety disorder. There are various diagnoses for the anxiety disorder, and specific definition and diagnosis criteria are set for each of them. Examples of the disorder belonging to anxiety disorder include panic disorder, specific phobia (acrophobic, hemophobia, ophidiophobia, or the like), social phobia, obsessive-compulsive disorder, post-traumatic stress disorder, generalized anxiety disorder, and acute stress disorder. As various mental disorders with different characteristics belong to the anxiety disorder, cause of the disorder is complex and cannot be defined in one word. In general, including the deficiency or excessiveness of a neurotransmitter in cranial nerves, which are responsible for processing emotions such as anxiety or depression, genetic predisposing factors, and a functional or structural change in brain as determined by brain imaging, or the like, even a social psychological aspect and a cognitive behavioral aspect relating to the analysis and determination of the previous experiences and newly-obtained information may serve as a cause of having excessive anxiety. In particular, the post-traumatic stress disorder and acute stress disorder mainly occur by having an accident or a disaster causing severe psychological shock as a cause of disorder.

*Fraxinus rhynchophylla* as one of the ashes grows on hillsides or in river valleys and it has height of 10 m and grayish brown tree bark with ash-colored white irregular patterns. The leaves are opposite, and odd-pinnately compound with 5 to 7 small leaves. The leaves have a wide baso (i.e., oriental lancet with long oval shape and sharp tip) shape with length of 6 to 15 cm and wavy serrated edges, and they have hairs not on the front side but on the vein in back side. *Fraxinus rhynchophylla* is dioecious but sometimes mixed with a bisexual flower, and it blooms in May. Flowers are arranged in the panicle inflorescence on the axils of leaves of young branch. The staminate flower has a stamen and a sepal, two for each, while the pistillate flower has a sepal, a stamen, and a pistil, 2 to 4 for each. The petals have an upside-down baso shape. It bears a samara fruit having length of 2 to 4 cm, which ripens in September. Fruit wing has a baso shape or a long baso shape. When the branches are soaked in water, the water turns a blue color, and thus the tree is called an "ash" tree. In oriental medicine, the tree bark (i.e., Fraxini cortex) is used a stomachic, an anti-inflammatory agent, or a astringent. *Fraxinus rhynchophylla* is found in Korea, China, or the like.

As a technique relating to an extract of *Fraxinus rhynchophylla*, in Korean Patent Application Laid-Open No. 2009-0072858, a technique relating to a composition for preventing and treating a brain disorder comprising a compound separated from Fraxini cortex as an effective ingredient is described. However, so far there is no disclosure of a composition for preventing, ameliorating, or treating depression and anxiety disorder comprising an extract of *Fraxinus rhynchophylla* as an effective ingredient as it is described in the present invention.

SUMMARY

The present invention is devised under the circumstances described above, and the present invention provides a composition for preventing, ameliorating, or treating depression and anxiety disorder comprising *Fraxinus rhynchophylla* extract as an effective ingredient. It is determined by an open field test and a forced swim test that, according to the administration of a *Fraxinus rhynchophylla* extract as an effective ingredient of the present invention, the anti-depressive effect is exhibited in an animal model with induced depression and anxiety disorder. Furthermore, a decrease in blood cortisol level and an increase in blood serotonin level, and also an increase in expression amount of pCERB, BDNF, and mBDNF proteins in hippocampal tissues are shown upon the administration of the extract, and the present invention is completed accordingly.

To achieve the purpose described above, the present invention provides a pharmaceutical composition for preventing or treating depression and anxiety disorder comprising an extract of *Fraxinus rhynchophylla* as an effective ingredient.

The present invention further provides a functional health food composition for preventing or ameliorating depression and anxiety disorder comprising an extract of *Fraxinus rhynchophylla* as an effective ingredient.

The present invention relates to a composition for preventing, ameliorating, or treating depression and anxiety disorder comprising *Fraxinus rhynchophylla* extract as an effective ingredient, in which the composition has an effect of improving the depressive behavior and low physical activity shown in an animal model with induced anxiety and depression, reducing the level of cortisol, increasing the level of serotonin, and also increasing the expression amount of pCERB, BDNF, and mBDNF proteins in hippocampal tissues.

DETAILED DESCRIPTION

Figure 1:
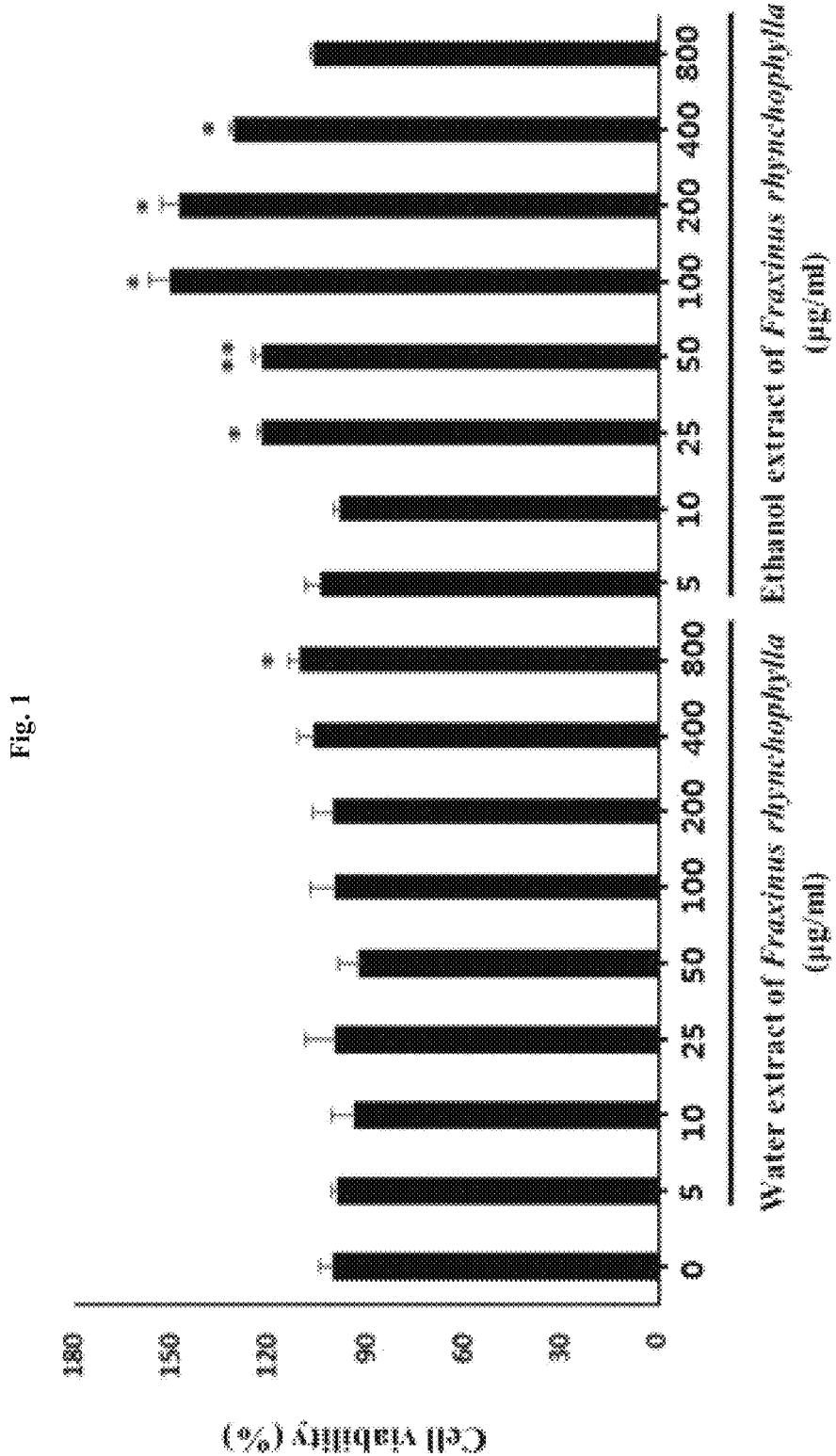
FIG. 1 shows the result of determining the cell viability (%) after treating PC12 cells, i.e., a rat neuronal cell line, with an ethanol extract of *Fraxinus rhynchophylla* or a water extract of *Fraxinus rhynchophylla* of the present invention at various concentrations (5, 10, 25, 50, 100, 200, 400, 800 μg/ml) for 24 hours. * and ** indicate that the cell viability (%) has increased in statistically significant sense compared to the normal group which has not been treated with an ethanol extract of *Fraxinus rhynchophylla*, in which *p<0.05 and **p<0.01.

The present invention relates to a pharmaceutical composition for preventing or treating depression and anxiety disorder comprising an extract of *Fraxinus rhynchophylla* as an effective ingredient.

The extract of *Fraxinus rhynchophylla* can be produced by a method including the following steps:

(1) adding an extraction solvent to *Fraxinus rhynchophylla* for extraction;

(2) filtering the extract of the step (1); and (3) concentrating and drying the filtered extract of the step (2) to produce an extract, but the method is not limited thereto.

The extraction solvent of the above step (1) is preferably selected from water, $C_1$-$C_4$ lower alcohol, and a mixture thereof, and it is more preferably ethanol, and even more preferably 70% (v/v) ethanol, but it is not limited thereto. With regard to the production method, any kind of common methods that are generally known as an extraction method in the pertinent art, e.g., filtration, hot water extraction, impregnation extraction, extraction by reflux condensation, and ultrasonic extraction, can be used. It is preferable that the extraction is carried out by adding an extraction solvent in an amount of 1 to 20 times the weight of dried *Fraxinus rhynchophylla*. More preferably, the extraction solvent is added in an amount of 5 to 15 times, and even more preferably added in an amount of 10 times the weight of dried *Fraxinus rhynchophylla*. The extraction temperature is preferably between 60° C. and 100° C., but it is not limited thereto. Furthermore, the extraction time is preferably between 1 hour and 48 hours, more preferably between 1 hour and 24 hours, and most preferably 3 hours, but it is not limited thereto. Concentration of the step (3) in the above method uses a vacuum rotary condenser or a vacuum rotary evaporator, but it is not limited thereto. Furthermore, the drying is preferably carried out by drying under reduced pressure, drying under vacuum, drying under boiling, spray drying, or freeze-drying. It is more preferably freeze-drying, but it is not limited thereto.

The extract of *Fraxinus rhynchophylla* is preferably a Fraxini cortex extract of stem bark or branch bark of *Fraxinus rhynchophylla*, but it is not limited thereto.

The anxiety disorder is preferably one or more selected from separation or isolation anxiety, paranoia, generalized anxiety disorder, generalized obsessive-compulsive disorder, anxiety neurosis, and panic disorder, but it is not limited thereto.

The pharmaceutical composition of the present invention may be prepared in various formulations including an oral formulation and a parenteral formulation. In case of formulating the composition, the formulation can be made by using a carrier, a vehicle, or a diluent that are commonly used for producing a preparation, but it is not limited thereto.

As for the solid preparation for oral administration, a tablet, a pill, a powder preparation, a granule, a capsule or the like are included, and such solid preparation is produced by mixing at least one compound with one or more vehicles such as starch, calcium carbonate, sucrose, lactose, or gelatin. Furthermore, other than simple vehicles, a lubricating agent such as magnesium stearate or talc is also used. For the liquid preparation for oral administration, a suspension, a solution preparation for internal use, an emulsion, a syrup preparation, or the like can be mentioned. Other than water or liquid paraffin as a commonly used simple diluent, various kinds of a vehicle such as moisturizing agent, sweetening agent, aromatic agent, or preservatives may be included.

Examples of a preparation for parenteral administration include a sterilized aqueous solution, a non-soluble agent, a suspension agent, an emulsion, a freeze-drying agent, and a suppository agent. As a water insoluble solvent or a suspending agent, propylene glycol, polyethylene glycol, or vegetable oil such as olive oil, and injectable ester such as ethylolate can be used. As a base for a suppository, WITEPSOL, macrogol, TWEEN 61, cacao fat, laurin fat, glycerol, gelatin, or the like can be used.

The pharmaceutical composition of the present invention can be administered either orally or parenterally. In case of parenteral administration, it is preferable to choose external application on skin, intraperitoneal, rectal, intravenous, muscular, subcutaneous, endometrium injection, or intracerebroventricular injection, but it is not limited thereto.

The pharmaceutical composition of the present invention is administered in a pharmaceutically effective amount. As described herein, the expression "pharmaceutically effective amount" means an amount sufficient for treating a disorder at reasonable benefit-risk ratio that can be applied for a medical treatment. The effective dose level may be determined based on a type or severeness of a disorder of a patient, activity of a pharmaceutical, sensitivity to a pharmaceutical, administration period, administration route, excretion ratio, time period for therapy, elements including a pharmaceutical used in combination, and other elements that are well known in the medical field. The composition of the present invention can be administered as a separate therapeutic agent, or it can be used in combination with other therapeutic agent. It can be administered in order or simultaneously with a conventional therapeutic agent. It can be also administered as single-dose or multi-dose. It is important to administer an amount which allows obtainment of the maximum effect with minimum dose while considering all of the aforementioned elements without having any side effect, and the dosage can be easily determined by a person skilled in the pertinent art.

The dosage of the composition of the present invention may vary depending on bodyweight, age, sex, health state, diet of a patient, administration period, administration method, excretion rate, and severeness of disorder. However, the daily dosage is, in terms of the amount of an extract of *Fraxinus rhynchophylla*, 0.01 to 1,000 mg/kg, preferably 30 to 500 mg/kg, and more preferably 50 to 300 mg/kg, and it can be administered 1 to 6 times per day. However, since the dosage may be increased or decreased depending on the administration route, severeness of a disorder, sex, body weight, age or the like, the scope of the present invention is not limited by the aforementioned dosage in any sense.

The present invention further relates to a functional health food composition for preventing or ameliorating depression and anxiety disorder comprising an extract of *Fraxinus rhynchophylla* as an effective ingredient.

The functional health food composition of the present invention comprising an extract of *Fraxinus rhynchophylla* as an effective ingredient may be directly added to a food product or used with other food product or food ingredient, and it can be suitably used according to a common method. The mixing amount of the effective ingredient can be suitably determined based on the purpose of use (i.e., prevention or amelioration). In general, the amount of an extract of *Fraxinus rhynchophylla* to be comprised in the functional health food composition can be 0.1 to 90 parts by weight relative to the total weight of the functional health food composition. However, in case of long-term consumption under the purpose of maintaining good health and hygiene or managing health, it can be an amount below the aforementioned range, and, as there is no problem in terms of safety, the effective ingredient may be also used in an amount above the aforementioned range.

When the functional health food composition of the present invention is consumed in the form of a beverage, other ingredients are not particularly limited except that, as an essential ingredient, the aforementioned extract of *Fraxinus rhynchophylla* is comprised at indicated ratio, and, like common beverages, various flavors or natural carbohydrates can be comprised as an additional component. Examples of the natural carbohydrates include monosaccharides such as glucose or fructose, disaccharides such as maltose or sucrose, polysaccharides such as dextrin or cyclodextrin, and sugar alcohols such as xylitol, sorbitol, or erythritol. As a flavor other than those described above, natural flavor (thaumatin, *stevia* extract (e.g., rebaudioside A and glycyrrhizin)) and synthetic flavor (e.g., saccharine and aspartame) can be advantageously used.

The functional health food composition of the present invention may further comprise, other than the effective ingredient, at least one selected from a nutritional supplement, a vitamin, an electrolyte, a flavor, a coloring agent, an enhancing agent, pectinic acid and a salt thereof, alginic acid and a salt thereof, an organic acid, a protective colloidal thickening agent, a pH adjusting agent, a stabilizer, a preservative, glycerin, alcohol, and a carbonating agent used for carbonated drink. Other than those, fruit flesh for producing natural fruit juice or vegetable drink can be comprised in the functional health food composition of the present invention. The fruit flesh may be used either independently or in combination thereof. Ratio of the above various additives is not critical, but it is generally selected from a range of about 0.1 to 20 parts by weight relative to 100 parts by weight of the extract of *Fraxinus rhynchophylla* of the present invention.

Hereinbelow, the present invention is explained in greater detail in view of the Examples. However, the following Examples are given only for specific explanation of the present invention and it would be evident to a person who has common knowledge in the pertinent art that the scope of the present invention is not limited by them.

EXAMPLES

Experimental Methods

1. Preparation of Extract of *Fraxinus rhynchophylla*

Reflux extraction of *Fraxinus rhynchophylla* was carried out by using 70% (v/v) ethanol which is 10 times the weight of *Fraxinus rhynchophylla* (2,500 g). After the extraction, the extract was filtered and concentrated under reduced pressure using a rotary vacuum condenser, and then subjected to freeze-drying to obtain an ethanol extract of *Fraxinus rhynchophylla* (130 g).

By adding water which is 10 times the weight of *Fraxinus rhynchophylla* (2,500 g), hot water extraction was carried out. After the extraction, the extract was filtered and concentrated under reduced pressure using a rotary vacuum condenser, and then subjected to freeze-drying to obtain a water extract of *Fraxinus rhynchophylla*.

2. In Vitro Depression Model

To carry out a cellular and molecular level study of the working mechanism related to corticosterone as a representative depression hormone, PC12 cells, i.e., a rat neuronal cell line, were treated with corticosterone.

PC12 cells used for this study were purchased from KCTC Biological Resource Center (Daejeon, S. Korea). PC12 cells were cultured in a 37° C., 5% $CO_2$ incubator by using RPMI-1640 (HyClone, Logan, Utah) medium containing 10% horse serum, 5% fetal bovine serum, penicillin (100 unit/ml), and streptomycin (100 μg/ml).

3. Induction of Cell Apoptosis and Analysis of Nerve Cell Protective Effect Against the Induction To determine the nerve cell protective effect of a water extract and an ethanol extract of *Fraxinus rhynchophylla*, PC12 cells were treated with the agent at various concentrations; normal control group (normal), corticosterone control group (control, 250 μM), group treated with corticosterone (250 μM)+water extract or ethanol extract of *Fraxinus rhynchophylla* (5 to 800 μg/ml), and, after 1 hour, the cells were treated with corticosterone. Furthermore, at least 4 hours before the treatment with water extract or ethanol extract of *Fraxinus rhynchophylla*, the medium was replaced with a serum-free medium.

4. Cell Viability Assay (WST Assay)

PC12 cells were applied to a 96-well plate in an amount of 100 μl for each well to have a concentration of 2×10⁵ cells/ml. After the stabilization for 24 hours, the medium was replaced with a serum-free medium. After 4 hours or so, the cells were treated with an ethanol extract or a water extract of *Fraxinus rhynchophylla* at various concentrations and cultured for 24 hours in a 37° C., 5% $CO_2$ incubator. Thereafter, WST (High Sensitive Water Soluble Tetrazolium Salt) assay was carried out (EZ-cytox, DoGenBio Co., Ltd., S. Korea).

Furthermore, 1 hour after the treatment with an ethanol extract or a water extract of *Fraxinus rhynchophylla* at various concentrations, the cells were treated with corticosterone (250 μM). Then, to the cells obtained after completion of the culture for 24 hours, a WST solution was added in an amount of 10 μl and the reaction was allowed to occur for 6 hours in an incubator. Absorbance at 450 nm was then measured by using a micro spectrophotometer (Molecular Device, Sunnyvale, Calif., USA).

5. Real-Time Gene Analysis (Real-Time PCR)

PC12 cells were applied to a 6-well plate in an amount of 2 ml for each well to have a concentration of 2×10⁵ cells/ml followed by a treatment with an ethanol extract or a water extract of *Fraxinus rhynchophylla* at various concentrations. After 1 hour, the cells were treated with corticosterone (250 μM) and cultured for 24 hours in a 37° C., 5% $CO_2$ incubator. Then, the medium was discarded and RNA was isolated by adding 500 μl of Tri-Reagent (Molecular Research Center, Cincinnati, Ohio). Preparation was made to have a quantified RNA amount of 600 ng, and then, by using PrimeScript RT reagent Kit (Takara Bio, Shiga, Japan), cDNA was synthesized according to the manufacturer's protocol. Real-time PCR was carried out by using thus-prepared cDNA, and Bax, Bcl-2, β-actin primers. The real-time PCR was carried out as follows by using 7500 Real-Time PCR System (Applied Biosystems, Inc., Foster City, Calif., USA); 50° C. for 2 minutes, 95° C. for 10 minutes, followed by 40 cycles at 95° C. for 15 seconds and 60° C. for 1 minute.

TABLE 1

Primer sequences for carrying out real-time PCR

| Gene | | Primer Sequences |
|---|---|---|
| β-Actin | sense | 5'-AGCAGATGTGGATCAGCAAG-3' (SEQ ID NO: 1) |
| | antisense | 3'-AACAGTCCGCCTAGAAGCAT-5' (SEQ ID NO: 2) |
| Bax | sense | 5'-ACACCTGAGCTGACCTTG-3' (SEQ ID NO: 3) |
| | antisense | 3'-AGCCCATGATGGTTCTGATC-5' (SEQ ID NO: 4) |
| Bcl-2 | sense | 5'-CATGCGACCTCTGTTTGA-3' (SEQ ID NO: 5) |
| | antisense | 3'-GTTTCATGGTCCATCCTTG-5' (SEQ ID NO: 6) |

6. Test for Protein Detection (Western Blots)

PC12 cells were applied to a 6-well plate to have a concentration of 5×10⁴ cells/ml. After the stabilization for 24 hours, the cells were treated with an ethanol extract or a water extract of *Fraxinus rhynchophylla* at various concentrations. After 1 hour, the cells were treated with corticosterone (250 μM) and cultured for 24 hours in a 37° C., 5% $CO_2$ incubator. Then, the medium was discarded, and the cells were washed with PBS and a cell lysate was obtained by using a lysis buffer. The lysate was separated on a SDS-page gel and transferred to a membrane followed by blocking. Then, a reaction with BDNF antibody was carried out for 16 hours at 4° C. followed by a reaction with HRP-conjugated secondary antibody at room temperature for 1 hour. The image was developed by using LAS-3000 image analyzer (Fuji Photo Film Co., Tokyo, Japan) and analyzed.

7. Administration

*Fraxinus rhynchophylla* extract was dissolved in physiological saline to have a concentration of 100 mg/kg for each, and then aliquoted. One hour before applying the stress for 14 days, the sample was administered via an oral route.

8. Animal Model with Induced Depression and Anxiety Disorder

A 7-week old male C57BL/6 mouse was acclimated for 1 week, and then exposed to a stress everyday between 10:00 to 14:00 o'clock. Specifically, 1 hour after the oral administration of a sample, an electric shock with strength of 0.5 mA was applied to the foot sole of the mouse for 1 sec with an interval of 10 seconds, for 2 minutes in total, by using a shuttle box (JD-SI-10, JEUNG DO BIO & PLANT CO, LTD, Seoul, S. Korea). After applying the electric shock, the mouse was put to a hemicylindrical restraining device (JD-R 05A, JEUNG DO BIO & PLANT CO, LTD, Seoul, S. Korea) made of 30 mm-thick acryl, one animal in each device, and then restrained in the immobile state for 2 hours.

Figure 5:
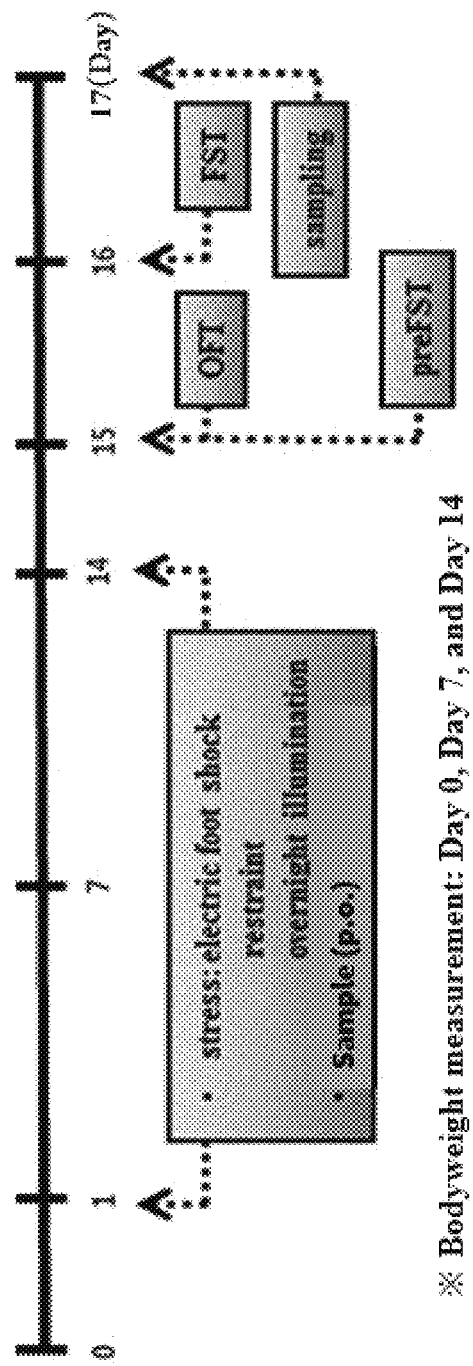
FIG. 5 illustrates a scheme for establishing an animal model with induced depression and anxiety disorder of the present invention, in which OFT represents an open field test and FST represents a forced swim test.

In addition, for the control group, the 12-hour day and night cycle was maintained, but light illumination was applied to the test group for 24 hours to disrupt the regular living pattern, and thus a sleep-interfering environment was created (FIG. 5).

9. Weight Change Determination

Figure 6:
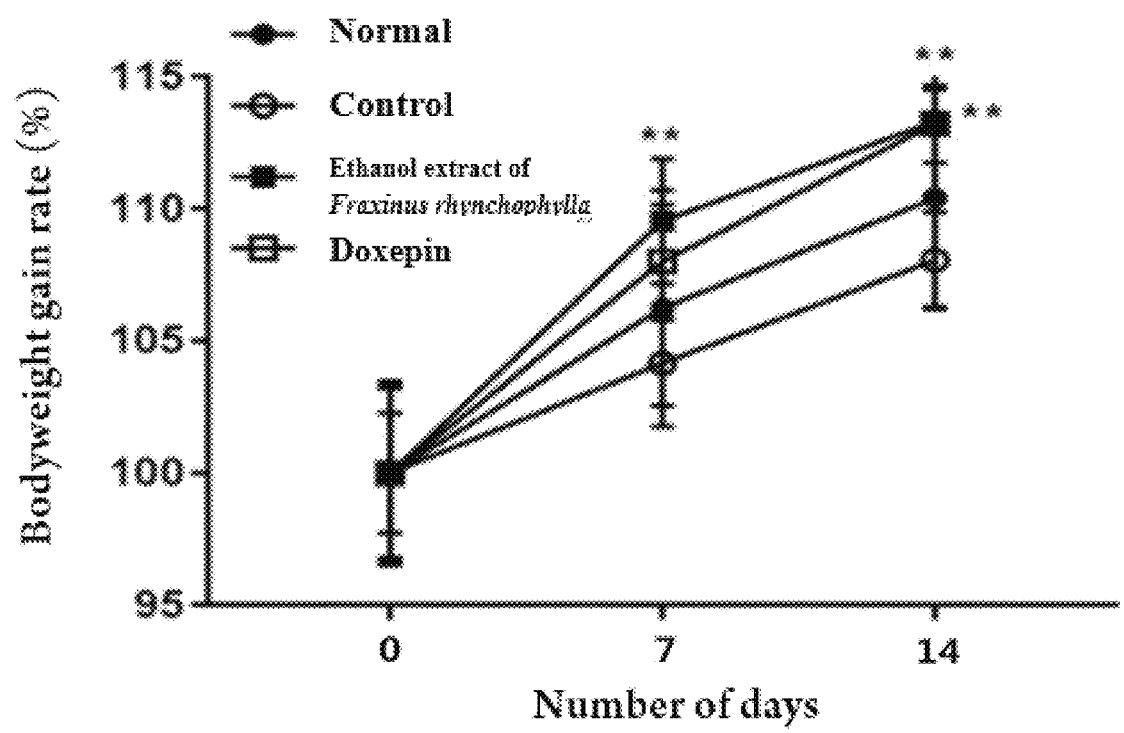
FIG. 6 shows the result of determining a change in the bodyweight of the animal before the administration (Day 0), or on Day 7 or Day 14 after the administration of 100 mg/kg ethanol extract of *Fraxinus rhynchophylla* of the present invention or 150 mg/kg doxepin to a c57BL/6 mouse which has been induced to have depression and anxiety disorder by electric shock, restraint, and sleep-disturbing stress. * and ** indicate that, compared to the control group, the bodyweight has increased in statistically significant sense in the group administered with the ethanol extract of *Fraxinus rhynchophylla* of the present invention or in the group administered with doxepin, in which *p<0.05, **p<0.01.

A change in body weight caused by administration of the ethanol extract of *Fraxinus rhynchophylla* of the present invention was determined in the animal model with induced depression and anxiety disorder. Specifically, the body-weight of a mouse was measured, before the exposure to stress (Day 0), or on Day 7 or Day 14 after the exposure to stress for the normal group, the control group (i.e., group induced with depression and anxiety disorder), the test group (i.e., group administered with the ethanol extract of *Fraxinus rhynchophylla* of the present invention), and the positive control group (i.e., group administered with doxepin) (FIG. 6).

10. Open Field Test (OFT)

Open field test is to determine the degree of anxiety, which is one symptom of depression, by measuring the voluntary movement of a mouse after entering an unfamiliar field for the first time. At the center (15 cm×15 cm) of an open box with a dimension of 30 cm×30 cm×30 cm, which is made of white acryl, a C57BL/6 mouse which has been induced to have depression and anxiety disorder was placed, and then total travel distance and frequency of center entry for 10 minutes were measured. For the measurement, after recording using a video camera, the overall movement of the C57BL/6 mouse was analyzed by using Video tracking software (SMART 3.0, Panlab, Spain).

11. Forced Swim Test (FST)

Forced swim test is a test to determine despair among the symptoms of depression, and the immobility of a mouse was checked using a cylinder having a depth which prevents the animal from touching its paws or tail to the floor of the cylinder. Specifically, a transparent acryl cylinder with a size of 18×50 cm was filled with water (25° C.) to a height of 30 cm, and a separate cylinder was used for each mouse. One day before the test, the mouse was exposed to water for 15 minutes for adaptation. On the day of test, the mouse was exposed to water for 6 minutes at the same conditions as the adaptation. Then, the immobility time during 4 minutes, i.e., excluding initial 2 minutes as adaptation period from the total 6 minutes, was measured.

12. Measurement of Cortisol Level in Blood Serum

The cortisol level in blood serum separated from each test animal was measured. Measurement of cortisol was carried out by competitive immunoenzyme assay using cortisol ELISA Kit (Cayman Chemical Company, Ann Arbor, Mich., USA). To 50 µl of a reference material or a sample (i.e., blood serum), a cortisol AChE tracer and an ELISA monoclonal antibody were added. After the overnight reaction at 4° C. followed by washing step, Ellman's reagent was added and stirring and reaction were carried out for 90 minutes at a rate of 500 rpm or less using an orbital stirrer. Absorbance at 405 nm was then measured.

13. Measurement of Change in Serotonin Level

The serotonin level in blood serum separated from each test animal was measured. First, according to the manual of Serotonin Elisa kit (Abcam, Cambridge, Mass.), the assay buffer solution was added in an amount of 150 µl to a non-specific binding well, 100 µl to Bo well, or 100 µl to a reference material well and a sample well of a goat anti-rabbit IgG microplate. Then, except the total activity well and blank well, serotonin alkaline phosphatase conjugate was added, 50 µl for each well. Except the blank well, total activity well, and non-specific binding well, a serotonin antibody was added to Bo, reference material, and test group. After stirring for 2 hours at 500 rpm, room temperature and washing 3 times, serotonin alkaline phosphatase conjugate, which has been diluted by 20 times, was added in an amount of 5 µl only to the total activity well. Finally, pNpp substrate solution was added in an amount of 200 µl for each followed by the reaction for 1 hour at room temperature without any stirring. The chromogenic reaction was terminated by using 50 µl reaction stop solution. Upon the completion of the reaction, absorbance at a wavelength of 405 nm was measured by using a microplate reader.

14. Measurement of Expression Amount of CREB, BDNF, and mBDNF Proteins in Hippocampal Tissues in Brain Protein expression pattern in brain hippocampal tissues which have been collected from each test animal was determined by Western blot analysis. The collected hippocampal tissues were homogenized by adding 300 µl of lysis buffer solution and centrifuged for 20 minutes at 13000 rpm to obtain the supernatant. After obtaining the protein amount in each sample, the protein was quantified to 1 µg/µl, and then the expression amount of protein was measured by using Mini PROTEAN TGX Gels.

15. Statistical Treatment

All data are expressed in means±standard deviation (means±SD). For the result of the following Example 1 to Example 4, the significance was determined by using an independent samples T test, and the significance determination was carried out at the level of P<0.05 or less (*p<0.05, p<0.01, *p<0.001).

In addition, for the statistical comparison of the results of Example 5 to Example 9, one-way measures analysis of variance (ANONA) was performed by post-hoc test (Bonferroni), and the significance determination was carried out at the level of p<0.05 (*p<0.05, p<0.01, *p<0.001).

Example 1. Effect of Water Extract or Ethanol Extract of *Fraxinus rhynchophylla* on Cell Viability and Cell Proliferation Performance of PC12 Cells Effect of a water extract or an ethanol extract of *Fraxinus rhynchophylla* on cell viability and cell proliferation performance of PC12 cells, i.e., a rat neuronal cell line, was determined.

According to the experimental methods that are described in the above, the cells were treated with a water extract or an ethanol extract of *Fraxinus rhynchophylla*, and the cell viability and cell proliferation performance (%) were determined. As a result, it was found that no cytotoxicity is shown in all test groups as illustrated in FIG. 1, and the cell proliferation performance (%) of significance was exhibited from the ethanol extract of *Fraxinus rhynchophylla* at a concentration of 25 to 400 µg/ml.

Example 2. Effect of Water Extract or Ethanol Extract of *Fraxinus rhynchophylla* on Nerve Cell Protection in PC12 Cells with Corticosterone-Induced Cell Apoptosis To determine the nerve cell protective effect of a water extract or an ethanol extract of *Fraxinus rhynchophylla* in PC12 cells with corticosterone-induced cell apoptosis, the cell viability and cell proliferation performance were analyzed.

Figure 2:
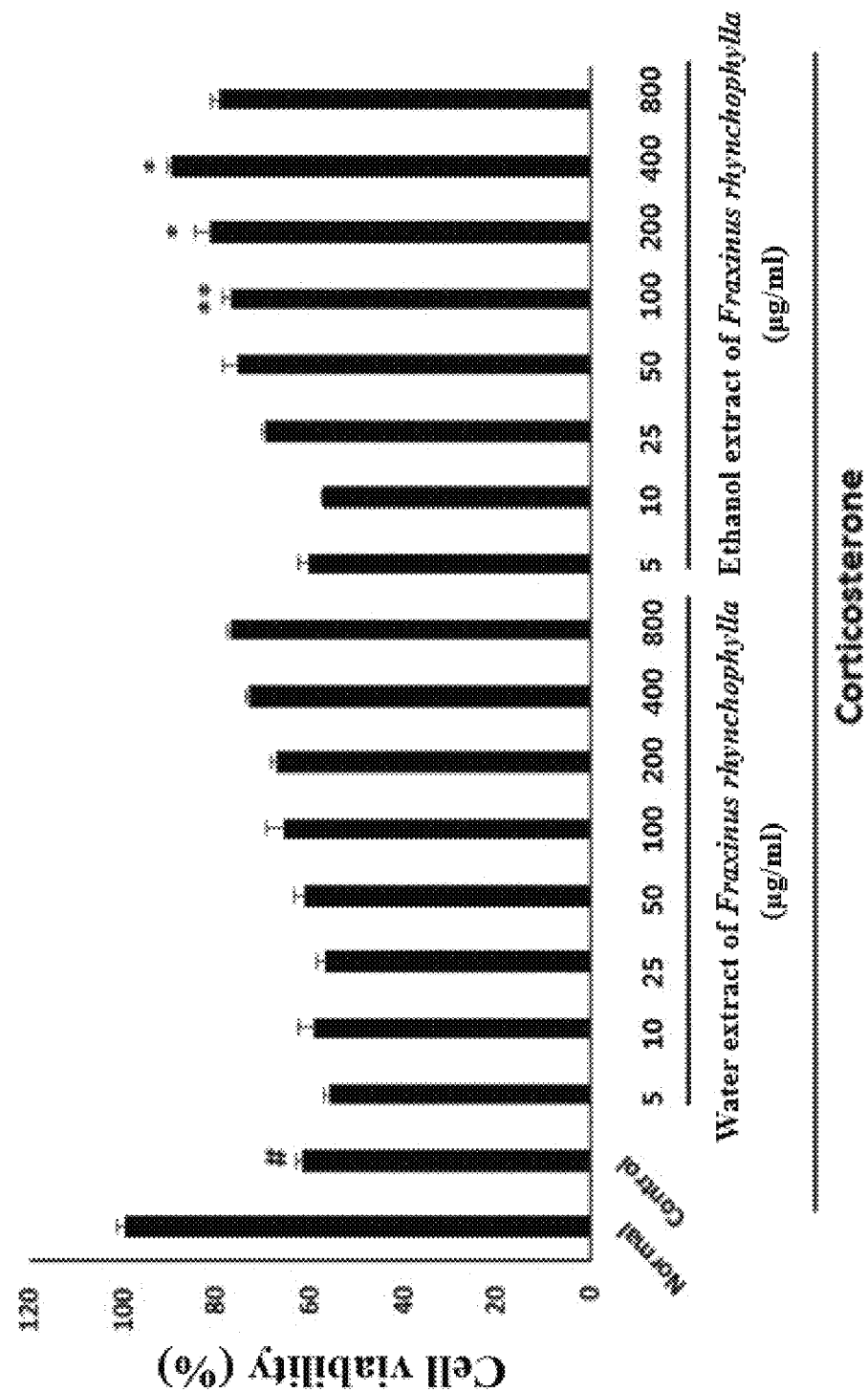
FIG. 2 shows the result of determining the cell viability (%) after treating PC12 cells, i.e., a rat neuronal cell line, with an ethanol extract of *Fraxinus rhynchophylla* or a water extract of *Fraxinus rhynchophylla* of the present invention at various concentrations (5, 10, 25, 50, 100, 200, 400, 800 μg/ml) and, after 1 hour, treating the cells with corticosterone for 24 hours to induce cell apoptosis. # indicates that the cell viability (%) has increased in statistically significant sense in the control group treated with corticosterone compared to the normal group which has not been treated with any, in which p<0.05. * and ** indicate that the cell viability has increased in statistically significant sense in the group treated with an ethanol extract of *Fraxinus rhynchophylla* compared to the control group, in which *p<0.05 and **p<0.01.

According to the experimental methods that are described in the above, the cells were treated with a water extract or an ethanol extract of *Fraxinus rhynchophylla*. One hour after the treatment, cell apoptosis was induced using corticosterone, and the cell viability and cell proliferation performance (%) were measured. As a result, as it is shown in FIG. 2, the cell proliferation performance (%) of significance was exhibited from the ethanol extract of *Fraxinus rhynchophylla* at a concentration of 100 to 400 µg/ml, but no such result of significance was exhibited from the water extract of *Fraxinus rhynchophylla*.

Example 3. Effect of Water Extract or Ethanol Extract of *Fraxinus rhynchophylla* on mRNA Expression of Cell Apoptosis Factor (Bax/Bcl2) in PC12 Cells with Corticosterone-Induced Cell Apoptosis In PC12 cells with corticosterone-induced cell apoptosis, the effect of a water extract or an ethanol extract of *Fraxinus rhynchophylla* on mRNA expression of cell apoptosis factor (Bax/Bcl2) was examined by real-time gene analysis.

Figure 3:
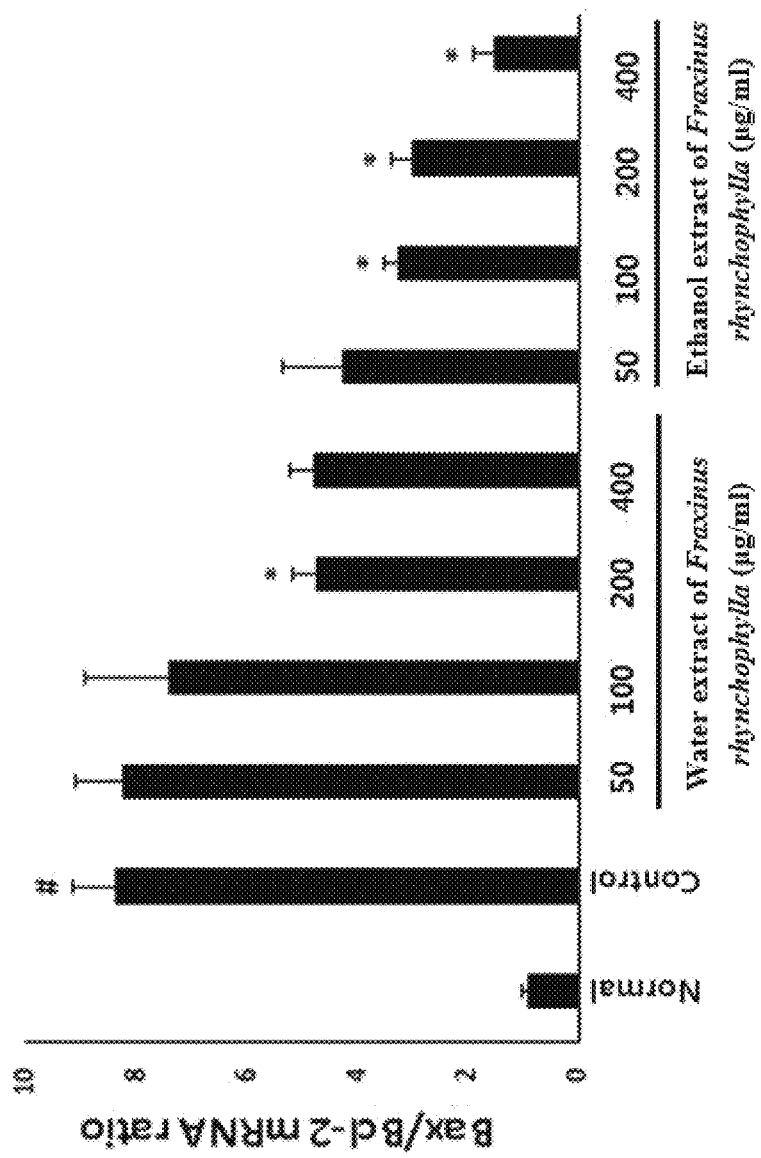
FIG. 3 shows the result of determining a change in the mRNA expression ratio of cell apoptosis factor (Bax/Bcl-2) after treating PC12 cells, i.e., a rat neuronal cell line, with an ethanol extract of *Fraxinus rhynchophylla* or a water extract of *Fraxinus rhynchophylla* of the present invention at various concentrations (50, 100, 200, 400 μg/ml) and, after 1 hour, treating the cells with corticosterone for 24 hours to induce cell apoptosis. # indicates that the mRNA expression ratio of Bax/Bcl-2 has increased in statistically significant sense in the control group treated with corticosterone compared to the normal group which has not been treated with any, in which p<0.05. * indicates that the mRNA expression ratio of Bax/Bcl-2 has decreased in statistically significant sense in the group treated with an ethanol extract or a water extract of *Fraxinus rhynchophylla* compared to the control group, in which p<0.05.

According to the experimental methods that are described in the above, one hour after the treatment with a water extract or an ethanol extract of *Fraxinus rhynchophylla*, cell apoptosis was induced using corticosterone, and the cell apoptosis factor was analyzed by real-time gene analysis. As a result, as it is shown in FIG. 3, it was found that the mRNA expression ratio of Bax/Bcl-2 has decreased in significant sense with 100 to 400 µg/ml ethanol extract of *Fraxinus rhynchophylla*. In case of the water extract of *Fraxinus rhynchophylla*, the mRNA expression ratio of Bax/Bcl-2 has decreased in significant sense only at the concentration of 200 µg/ml. Accordingly, it was determined that the ethanol extract of *Fraxinus rhynchophylla* exhibits a more effective influence on the mRNA expression of cell apoptosis factor (Bax/Bcl2) than the water extract of *Fraxinus rhynchophylla*.

Example 4. Effect of Water Extract or Ethanol Extract of *Fraxinus rhynchophylla* on Expression of Brain Derived Neurotrophic Factor (BDNF) in PC12 Cells with Corticosterone-Induced Cell Apoptosis It is known that the expression of brain derived neurotrophic factor (BDNF) is related to an onset of a cognitive disorder like depression (Naert, G., G. Ixart, T. Maurice, L. Tapia-Arancibia, and L. Givalois. 2011. Brain-derived neurotrophic factor and hypothalamic-pituitary-adrenal axis adaptation processes in a depressive-like state induced by chronic restraint stress. Mol. Cell Neurosci. 46: 55-66). Thus, in this Example 4, the effect of a water extract or an ethanol extract of *Fraxinus rhynchophylla* on the expression of BDNF was determined. Specifically, the effect of a water extract or an ethanol extract of *Fraxinus rhynchophylla* on the expression of BDNF in PC12 cells with corticosterone-induced cell apoptosis was determined by carrying out a protein detection method.

Figure 4:
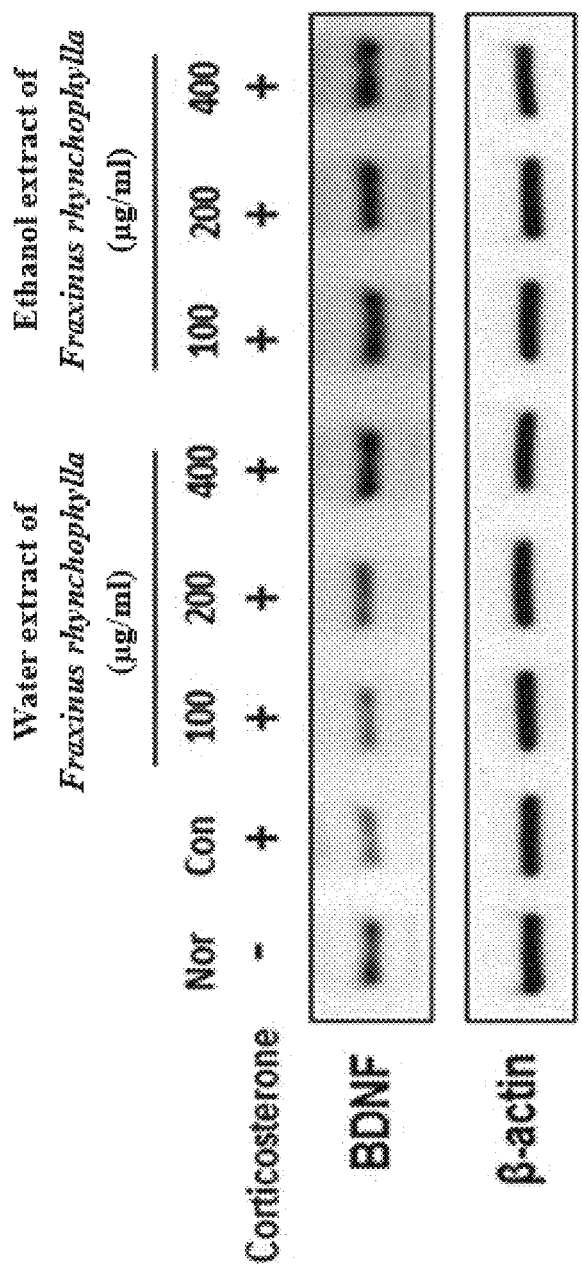
FIG. 4 shows the result of determining a change in the expression amount of BDNF after treating PC12 cells, i.e., a rat neuronal cell line, with an ethanol extract of *Fraxinus rhynchophylla* or a water extract of *Fraxinus rhynchophylla* of the present invention at various concentrations (100, 200, 400 μg/ml) and, after 1 hour, treating the cells with corticosterone for 24 hours to induce cell apoptosis.

One hour after the treatment with a water extract or an ethanol extract of *Fraxinus rhynchophylla*, cell apoptosis was induced using corticosterone, and BDNF was tested by a protein detection method. As a result, as it is shown in FIG. 4, it was found that the expression of BDNF has increased in significant sense with 100 to 400 μg/ml ethanol extract of *Fraxinus rhynchophylla*.

Taken together the results of Example 1 to Example 4 described above, it is found that, when PC12 cells as a rat neuronal cell line are treated with a water extract or an ethanol extract of *Fraxinus rhynchophylla* followed by induction of cell apoptosis using corticosterone, the cell viability (%) is enhanced, the cell apoptosis factor (Bax/Bcl-2) is reduced, and BDNF is increased by an extract of *Fraxinus rhynchophylla*, and, in particular, more excellent effect was obtained with an ethanol extract than a water extract of *Fraxinus rhynchophylla*. As such, for the following animal tests (in vivo test), only the ethanol extract of *Fraxinus rhynchophylla* shown to have a relatively higher effect was used to carry out the tests.

Example 5. Determination of Bodyweight Change

Because a long-term stress may exhibit an influence on the bodyweight of an animal, the bodyweight of the mouse was measured once a week. By setting the weight measured before applying the stress at 100 for each test group, the gain rate was expressed for all bodyweights.

As a result, as it is shown in FIG. 6, all the test groups tend to show an increase in bodyweight over time compared to the bodyweight before inducing depression and anxiety disorder by stress. On Day 7 and Day 14 after inducing depression and anxiety disorder, the control group showed a lower bodyweight gain rate compared to the normal group as it is induced to have the depression and anxiety disorder. However, the bodyweight of the test group to which 100 mg/kg ethanol extract of *Fraxinus rhynchophylla* has been administered showed a statistically significant increase compared to the control group.

Example 6. Effect of Administration of *Fraxinus rhynchophylla* Extract on Depression and Anxiety-Related Behavior in C57BL/6 Mouse with Induced Depression and Anxiety Disorder 1) Open Field Test Once exposed to a new environment, a normal healthy mouse starts to investigate the environment. But with a depression symptom, the mouse just circles around the edge or stays still due to the anxiety, and thus, by taking advantage of such properties, an open field test was carried out. Specifically, at the center of an open field with an area of 30 cm×30 cm, a center zone with a size of 15 cm×15 cm was designated, and the travel distance within this zone and number of entries made to this zone were examined.

Figure 7:
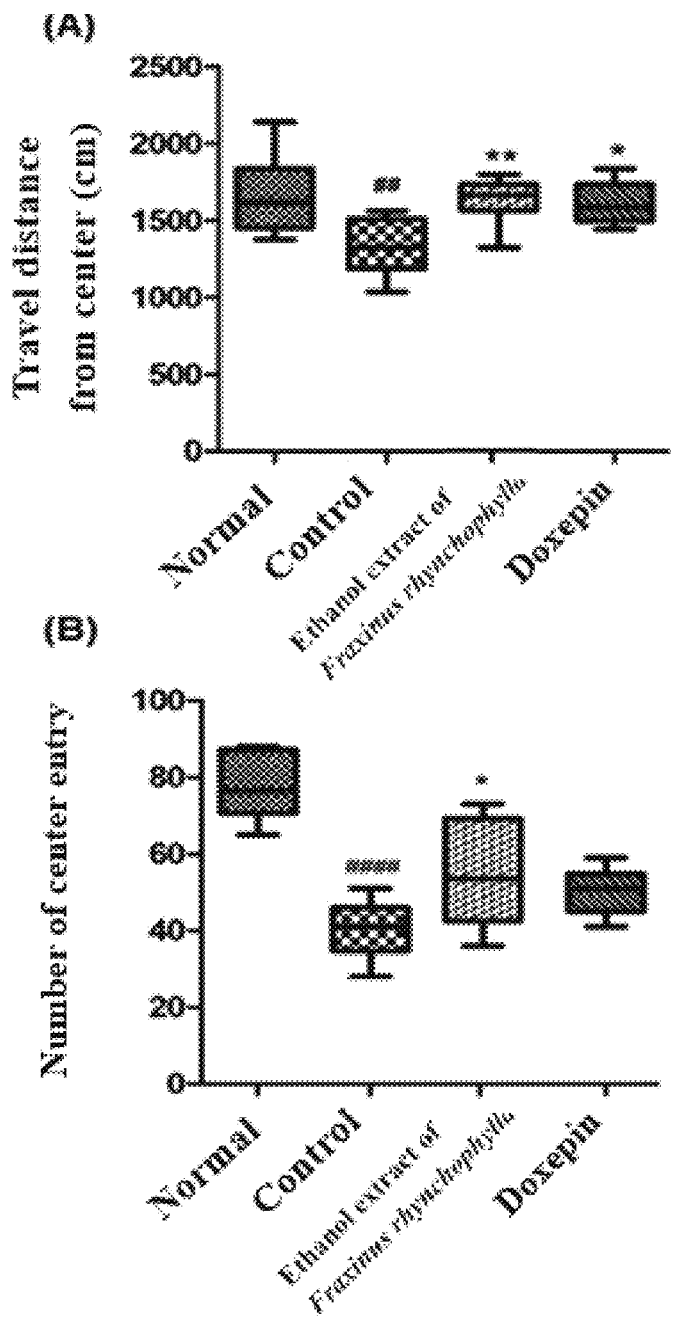
FIG. 7 shows the result of an open field test after administering for 14 days 100 mg/kg ethanol extract of *Fraxinus rhynchophylla* of the present invention or 150 mg/kg doxepin to a c57BL/6 mouse which has been induced to have depression and anxiety disorder by electric shock, restraint, and sleep-disturbing stress, and then carrying out the open field test on Day 15. ## and #### indicate that the travel distance from center (A) and the number of center entry (B) have decreased in statistically significant sense in the control group compared to the normal group, in which ##p<0.01, ####p<0.0001. * and ** indicate that the travel distance from center (A) and the number of center entry (B) have increased in statistically significant sense in the group administered with an ethanol extract of *Fraxinus rhynchophylla* of the present invention or doxepin compared to the control group, in which *p<0.05, *p<0.01.

As shown in A of FIG. 7, as a result of analyzing the travel distance within the center zone, the travel distance has decreased in statistically significant sense in the control group (i.e., control) compared to the normal group (i.e., normal). In the group administered with 100 mg/kg ethanol extract of *Fraxinus rhynchophylla* of the present invention, the travel distance within the center zone has increased in statistically significant sense. Similarly, in the group administered with 150 mg/kg doxepin as a positive control group, an increase in statistically significant sense was also shown.

Furthermore, as shown in B of FIG. 7, the number of entering the center zone departing from the edge is smaller in significant sense in the control group compared to the normal group. In the group administered with 100 mg/kg Fraxini cortex extract of branch bark of *Fraxinus rhynchophylla*, the number of entering the center zone has increased in significant sense.

2) Forced Swim Test

Figure 8:
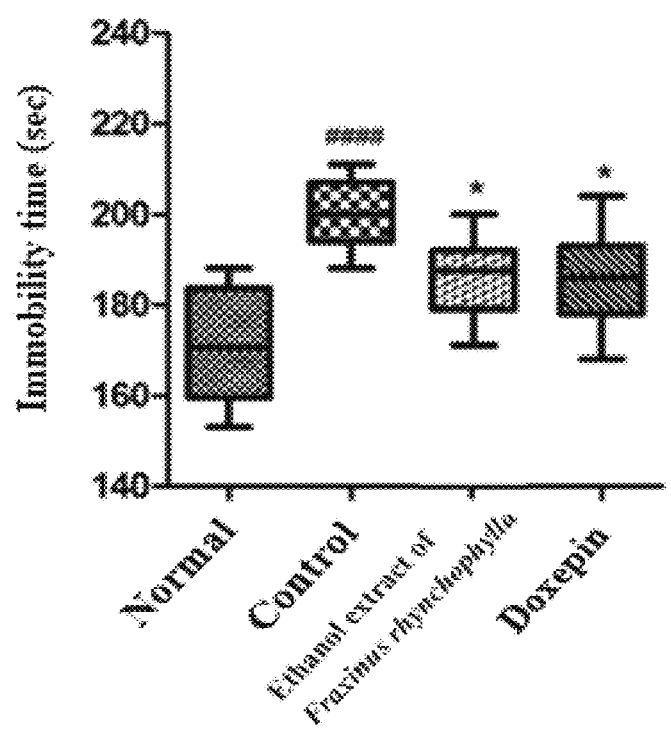
FIG. 8 shows the result of a forced swim test after administering for 14 days 100 mg/kg ethanol extract of *Fraxinus rhynchophylla* of the present invention or 150 mg/kg doxepin to a c57BL/6 mouse which has been induced to have depression and anxiety disorder by electric shock, restraint, and sleep-disturbing stress, and then carrying out the forced swim test on Day 15. #### indicates that the immobility time has increased in statistically significant sense in the control group compared to the normal group, in which p<0.0001. * indicates that the immobility time has decreased in statistically significant sense in the group administered with an ethanol extract of *Fraxinus rhynchophylla* of the present invention or doxepin compared to the control group, in which p<0.05.

In an unescapable water bath, a normal healthy mouse shows a behavior like swimming or climbing. However, with a symptom of depression, the mouse becomes lethargic, and thus shows a tendency of quickly giving up the behavior like swimming or climbing As shown in FIG. 8, as a result of performing a force swim test, the control group showed the immobility time which has increased in significant sense compared to the normal group. In the group administered with 100 mg/kg Fraxini cortex extract of branch bark of *Fraxinus rhynchophylla*, it was found that the immobility time has decreased in statistically significant sense, and the group administered with doxepin as a positive control group also showed the immobility time which has decreased in statistically significant sense.

Example 7. Determination of Change in Cortisol Hormone Level According to Administration of Ethanol Extract of *Fraxinus rhynchophylla* to C57BL/6 Mouse with Induced Depression and Anxiety Disorder Cortisol is a stress hormone which is secreted from adrenal cortex such that a human body can generate the maximum energy to fight against external stimulations like stress, and it plays a role of secreting more blood to an individual organ. When excessive or chronic stress is applied, cortisol is secreted in an excess amount to yield an increased blood concentration. In Example 7, the cortisol level in blood was measured by using an ELISA assay kit.

Figure 9:
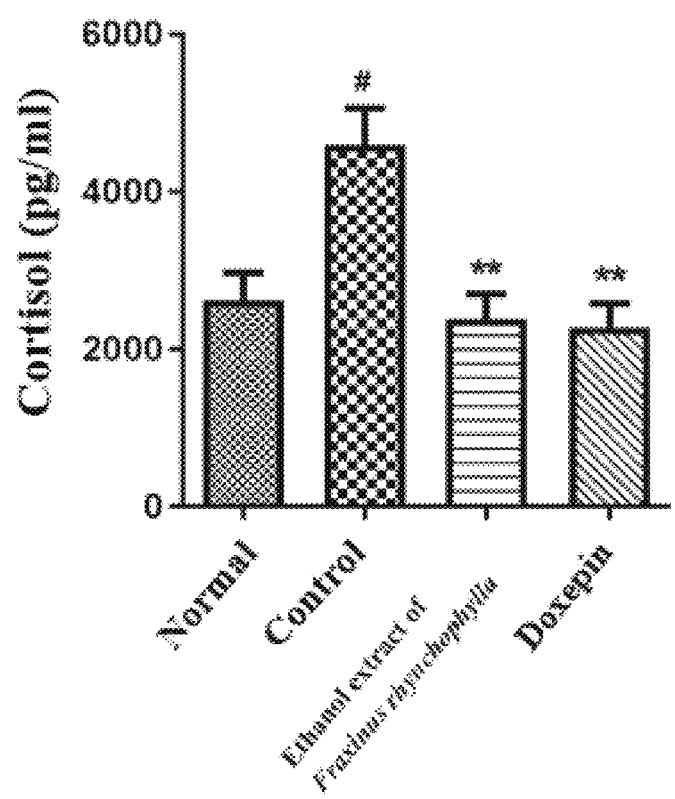
FIG. 9 shows the result of determining, by an immunoenzyme assay, the cortisol level in blood of c57BL/6 mouse after administering for 14 days 100 mg/kg ethanol extract of *Fraxinus rhynchophylla* of the present invention or 150 mg/kg doxepin to a c57BL/6 mouse which has been induced to have depression and anxiety disorder by electric shock, restraint, and sleep-disturbing stress, and then collecting the blood on Day 17. # indicates that the blood cortisol level has increased in statistically significant sense in the control group compared to the normal group, in which p<0.05. ** indicates that the blood cortisol level has decreased in statistically significant sense in the group administered with an ethanol extract of *Fraxinus rhynchophylla* of the present invention or doxepin compared to the control group, in which p<0.01.

As a result, as it is shown in FIG. 9, the cortisol level in blood has increased in significant sense in the control group compared to the normal group. In the group administered with 100 mg/kg Fraxini cortex extract of branch bark of *Fraxinus rhynchophylla*, the cortisol level in blood has decreased in statistically significant sense.

Figure 10:
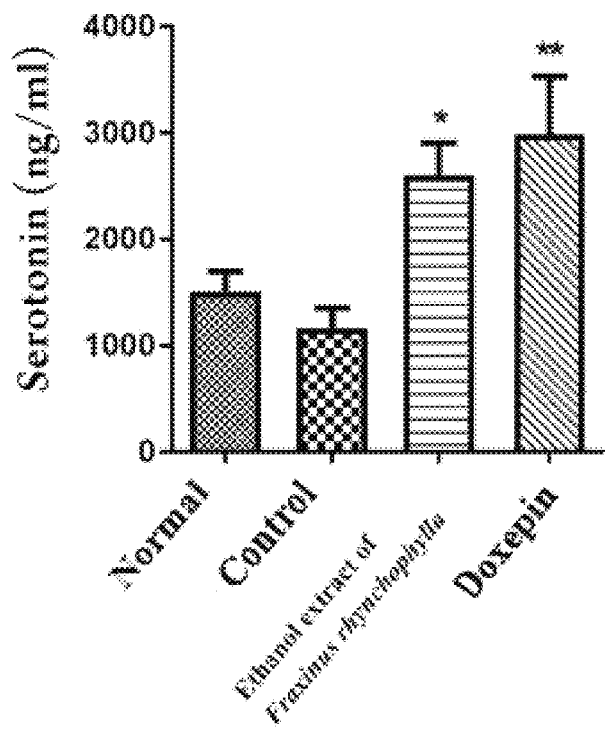
FIG. 10 shows the result of determining, by an immunoenzyme assay, the serotonin level in blood of c57BL/6 mouse after administering for 14 days 100 mg/kg ethanol extract of *Fraxinus rhynchophylla* of the present invention or 150 mg/kg doxepin to a c57BL/6 mouse which has been induced to have depression and anxiety disorder by electric shock, restraint, and sleep-disturbing stress, and then collecting the blood on Day 17. * and ** indicate that the blood serotonin level has increased in statistically significant sense in the group administered with an ethanol extract of *Fraxinus rhynchophylla* of the present invention or doxepin compared to the control group, in which *p<0.05, **p<0.01.

Example 8. Determination of Change in Serotonin Hormone Level According to Administration of Ethanol Extract of *Fraxinus rhynchophylla* to C57BL/6 Mouse with Induced Depression and Anxiety Disorder As a result of measuring the serotonin hormone level in blood, as it is shown in FIG. 10, the serotonin level has increased in statistically significant sense in the group administered with 100 mg/kg ethanol extract of *Fraxinus rhynchophylla* compared to the control group. In the group administered with doxepin as a positive control group, the serotonin hormone level has also increased in statistically significant sense.

Example 9. Effect on Expression Amount of Protein in Hippocampal Tissue (1) Determination of Expression Ratio of pCREB Protein in Hippocampal Tissues To determine the activation degree of CREB protein to pCREB protein, the expression ratio of phosphorylated pCREB was determined based on the expression amount of CREB protein in all groups (i.e., normal group, control group, test group, and positive control group), and, by having the expression ratio of pCREB in the normal group as a reference, the expression ratio was decided for each group.

Figure 11:
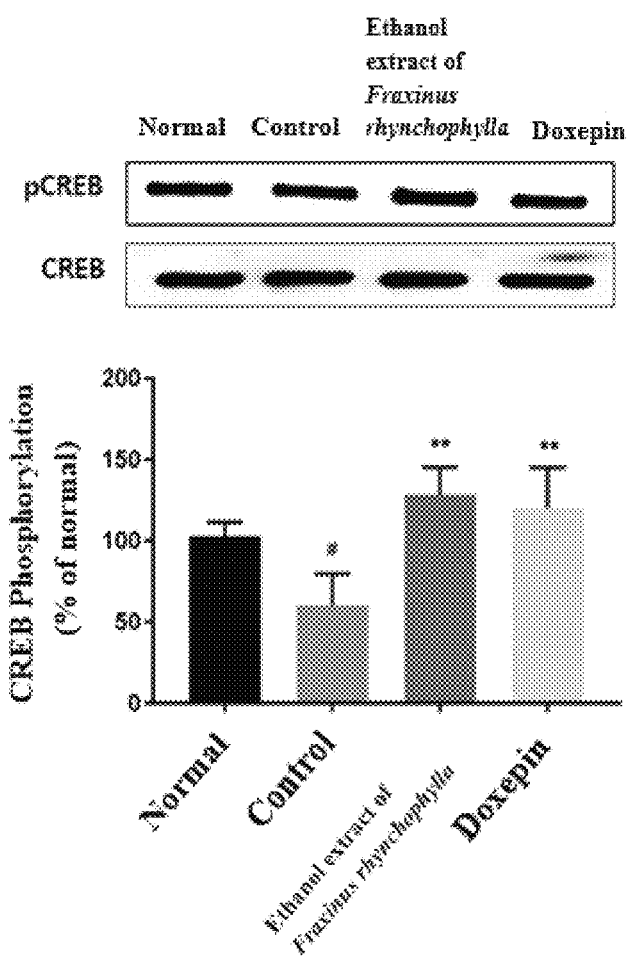
FIG. 11 shows the result of determining, by Western blot, CREB and pCREB in the hippocampal tissues of c57BL/6 mouse after administering for 14 days 100 mg/kg ethanol extract of *Fraxinus rhynchophylla* of the present invention or 150 mg/kg doxepin to a c57BL/6 mouse which has been induced to have depression and anxiety disorder by electric shock, restraint, and sleep-disturbing stress, and then collecting the hippocampal tissues on Day 17. # indicates that the phosphorylation of CREB has decreased in statistically significant sense in the control group compared to the normal group, in which p<0.05. ** indicates that the phosphorylation of CREB has increased in statistically significant sense in the group administered with an ethanol extract of *Fraxinus rhynchophylla* of the present invention or doxepin compared to the control group, in which p<0.01.

As a result, as it is shown in FIG. 11, the expression ratio of pCREB protein has decreased in statistically significant sense in the control group compared to the normal group. In the group administered with 100 mg/kg ethanol extract of *Fraxinus rhynchophylla* of the present invention, there was an increase in statistically significant sense compared to the control group. Similarly, in the group administered with 150 mg/kg doxepin as a positive control group, an increase in statistically significant sense was also shown.

(2) Determination of Expression of BDNF and mBDNF in Hippocampal Tissues

Figure 12:
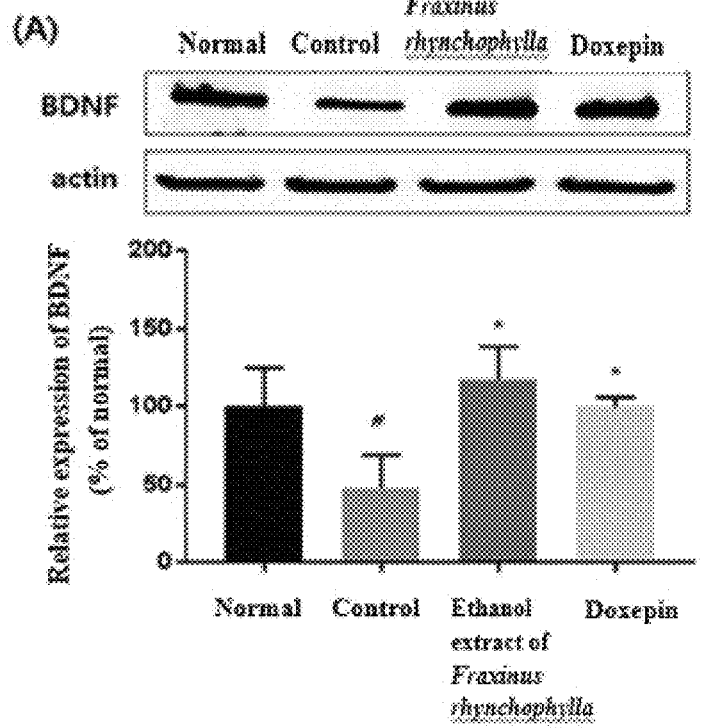
FIG. 12 shows the result of determining, by Western blot, BDNF and mBDNF in the hippocampal tissues of c57BL/6 mouse after administering for 14 days 100 mg/kg ethanol extract of *Fraxinus rhynchophylla* of the present invention or 150 mg/kg doxepin to a c57BL/6 mouse which has been induced to have depression and anxiety disorder by electric shock, restraint, and sleep-disturbing stress, and then collecting the hippocampal tissues on Day 17. # and ## indicate that the expression amount of BDNF and mBDNF has decreased in statistically significant sense in the control group compared to the normal group, in which # p<0.05, ## p<0.01. * indicates that the expression amount of BDNF and mBDNF has increased in statistically significant sense in the group administered with an ethanol extract of *Fraxinus rhynchophylla* of the present invention or doxepin compared to the control group, in which p<0.05.
Figure 12:
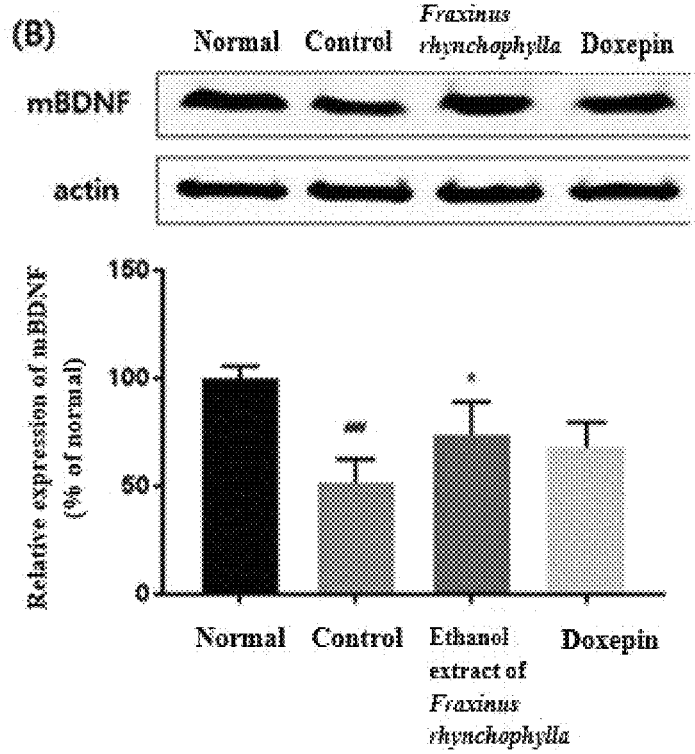

As a result of determining the relative expression amount of BDNF and mBDNF, as it is shown in FIG. 12, the expression amount of BDNF and mBDNF has decreased in statistically significant sense in the control group compared to the normal group. In the group administered with 100 mg/kg ethanol extract of *Fraxinus rhynchophylla* of the present invention, an increase in statistically significant sense was shown compared to the control group. Similarly, in the group administered with 150 mg/kg doxepin as a positive control group, an increase in statistically significant sense was also shown.

A sequence listing electronically submitted with the present application on Apr. 10, 2020 as an ASCII text file named 20200410_Q28920GR05_TU_SEQ, created on Apr. 6, 2020 and having a size of 2000 bytes, is incorporated herein by reference in its entirety.

---

The invention claimed is:

1. A method for treating at least one of depression and anxiety disorder caused by at least one of a reduced serotonin level and an increased cortisol level, the method comprising administering to a subject in need thereof an effective amount of a composition comprising an extract of *Fraxinus rhynchophylla* as an effective ingredient to increase serotonin level and/or to reduce cortisol level in blood of the subject.

2. The method of claim 1, wherein the extract of *Fraxinus rhynchophylla* is prepared by extracting the *Fraxinus rhynchophylla* with a solvent selected from the group consisting of water, a C1-C4 lower alcohol, and a mixture thereof.

3. The method of claim 1, wherein the extract of *Fraxinus rhynchophylla* is prepared by extracting the *Fraxinus rhynchophylla* with water.

4. The method of claim 1, wherein the extract of *Fraxinus rhynchophylla* is prepared by extracting the *Fraxinus rhynchophylla* with ethanol.

5. The method of claim 1, wherein the extract of *Fraxinus rhynchophylla* is a Fraxini cortex extract of stem bark or branch bark of *Fraxinus rhynchophylla*.

6. The method of claim 1, wherein the method is for treating the depression.

7. The method of claim 1, wherein the method is for treating the anxiety disorder.

8. The method of claim 1, wherein the method is for treating the depression and the anxiety disorder.

9. The method of claim 8, wherein the anxiety disorder is selected from the group consisting of a separation anxiety disorder, an isolation anxiety disorder, paranoia, a generalized anxiety disorder, a generalized obsessive-compulsive disorder, anxiety neurosis, a panic disorder, and a combination thereof.

10. The method of claim 1, wherein the composition is a pharmaceutical composition further comprising at least one selected from the group consisting of a carrier, a vehicle, a diluent, and a combination thereof.

11. The method of claim 1, wherein the composition is included in a food supplement further comprising at least one selected from the group consisting of a nutritional supplement, a vitamin, an electrolyte, a flavor, a coloring agent, an enhancing agent, pectinic acid, a salt of pectinic acid, alginic acid, a salt of alginic acid, an organic acid, a protective colloidal thickening agent, a pH adjusting agent, a stabilizer, a preservative, glycerin, alcohol, a carbonating agent, and a combination thereof.

12. A method for treating a subject having at least one of depression and anxiety disorder caused by at least one of a reduced serotonin level and an increased cortisol level, the method comprising:
preparing a composition comprising an extract of *Fraxinus rhynchophylla* produced by extracting the *Fraxinus rhynchophylla* with a solvent selected from the group consisting of water, a C1-C4 lower alcohol, and a mixture thereof; and
administering an effective amount of the composition to the subject to increase serotonin level and/or to reduce cortisol level in blood of the subject.

13. The method of claim 12, wherein the solvent is water.

14. The method of claim 12, wherein the solvent is ethanol.

15. The method of claim 12, wherein the *Fraxinus rhynchophylla* is a stem bark or a branch bark of the *Fraxinus rhynchophylla*.

16. The method of claim 12, wherein the subject has depression.

17. The method of claim 12, wherein the subject has the anxiety disorder selected from the group consisting of a separation anxiety disorder, an isolation anxiety disorder, paranoia, a generalized anxiety disorder, a generalized obsessive-compulsive disorder, anxiety neurosis, a panic disorder, and a combination thereof.

18. The method of claim 12, wherein the composition is a pharmaceutical composition further comprising at least one selected from the group consisting of a carrier, a vehicle, a diluent, and a combination thereof.

19. The method of claim 12, wherein the composition is included in a food supplement further comprising at least one selected from the group consisting of a nutritional supplement, a vitamin, an electrolyte, a flavor, a coloring agent, pectinic acid, a salt of pectinic acid, alginic acid, a salt of alginic acid, an organic acid, a protective colloidal thickening agent, a pH adjusting agent, a stabilizer, a preservative, glycerin, alcohol, a carbonating agent, and a combination thereof.

* * * * *

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: actin sense primer

<400> SEQUENCE: 1
agcagatgtg gatcagcaag                                               20

<210> SEQ ID NO 2
<211> LENGTH: 20
<212> TYPE: DNA
<213> ORGANISM: Artificial Sequence
<220> FEATURE:
<223> OTHER INFORMATION: actin antisense primer

<400> SEQUENCE: 2
aacagtccgc ctagaagcat                                               20

<210> SEQ ID NO 3
<211> LENGTH: 18
<212> TYPE: DNA
<213> ORGANISM: Artificial Sequence
<220> FEATURE:
<223> OTHER INFORMATION: Bax sense primer

<400> SEQUENCE: 3
acacctgagc tgaccttg                                                 18

<210> SEQ ID NO 4
<211> LENGTH: 20
<212> TYPE: DNA
<213> ORGANISM: Artificial Sequence
```

```
<220> FEATURE:
<223> OTHER INFORMATION: Bax antisense primer

<400> SEQUENCE: 4
agcccatgat ggttctgatc                                               20

<210> SEQ ID NO 5
<211> LENGTH: 18
<212> TYPE: DNA
<213> ORGANISM: Artificial Sequence
<220> FEATURE:
<223> OTHER INFORMATION: Bcl-2 sense primer

<400> SEQUENCE: 5
catgcgacct ctgtttga                                                 18

<210> SEQ ID NO 6
<211> LENGTH: 19
<212> TYPE: DNA
<213> ORGANISM: Artificial Sequence
<220> FEATURE:
<223> OTHER INFORMATION: Bcl-2 antisense primer

<400> SEQUENCE: 6
gtttcatggt ccatccttg                                                19
```